United States Patent  
Micinski et al.

(10) Patent No.: US 8,742,327 B2  
(45) Date of Patent: Jun. 3, 2014

(54) METHOD OF DETERMINING AUTO-CALIBRATION OF A TEST SENSOR

(71) Applicant: Bayer HealthCare LLC, Whippany, NJ (US)

(72) Inventors: Russell J Micinski, South Bend, IN (US); Andrew J Dosmann, Granger, IN (US); Steven C Charlton, Osceola, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 14/051,132

(22) Filed: Oct. 10, 2013

(65) Prior Publication Data
US 2014/0067309 A1 Mar. 6, 2014

Related U.S. Application Data

(63) Continuation of application No. 13/125,126, filed as application No. PCT/US2009/061472 on Oct. 21, 2009, now Pat. No. 8,586,911.

(60) Provisional application No. 61/196,859, filed on Oct. 21, 2008.

(51) Int. Cl.
*G12B 13/00* (2006.01)
*G01N 21/27* (2006.01)
*A61B 5/1495* (2006.01)

(52) U.S. Cl.
CPC ............ *G01N 21/274* (2013.01); *A61B 5/1495* (2013.01)
USPC .................................... 250/252.1

(58) Field of Classification Search
CPC . A61B 5/1495; G01J 1/58; G01N 2021/8494; G01N 2021/8645; G01N 21/274; G01N 21/278; G01N 21/64; G01N 21/645; G01N 21/8483; G01N 2201/12746; G01N 33/48771
USPC ............... 250/252.1; 356/432, 51; 702/40, 85
See application file for complete search history.

(56) References Cited

U.S. PATENT DOCUMENTS 3,907,503 A 9/1975 Betts et al.
4,714,874 A 12/1987 Morris et al.
(Continued)

FOREIGN PATENT DOCUMENTS

EP 0 887 421 A1 12/1998
EP 0 887 421 B1 3/2003
(Continued)

OTHER PUBLICATIONS

Written Opinion corresponding to International Patent Application No. PCT/US2009/061472, European Patent Office, dated Sep. 13, 2009, 3 pages.

(Continued)

*Primary Examiner* — Mark R Gaworecki
(74) *Attorney, Agent, or Firm* — Nixon Peabody LLP

(57) ABSTRACT

A method of determining auto-calibrating information of a test sensor includes providing an optical read head that includes a light source, a light guide and a detector. The read head forms an opening that is sized to receive a test sensor. The detector includes a linear-detector array or single detector. A test sensor is provided having apertures formed therein. The test sensor is placed in the opening of the optical read head. Light is transmitted from the light source through the apertures. The light transmitted through the apertures using the detector or detecting the absence of light being transmitted through the test sensor using the detector is detected. The detected light or the absence of detected light information from the detector is used to determine the auto-calibration information of the test sensor.

18 Claims, 9 Drawing Sheets

(56) References Cited

U.S. PATENT DOCUMENTS

| | | | |
|---|---|---|---|
| 5,194,393 A | 3/1993 | Hugl et al. |
| 5,305,233 A | 4/1994 | Kawagoe et al. |
| 5,408,535 A | 4/1995 | Howard et al. |
| 5,489,414 A | 2/1996 | Schreiber et al. |
| 5,518,689 A | 5/1996 | Dosmann et al. |
| 5,597,532 A | 1/1997 | Connolly |
| 5,611,999 A | 3/1997 | Dosmann et al. |
| 5,780,304 A | 7/1998 | Matzinger et al. |
| 5,866,349 A | 2/1999 | Lilja et al. |
| 5,945,341 A | 8/1999 | Howard, III |
| 5,962,215 A | 10/1999 | Douglas et al. |
| 6,168,957 B1 | 1/2001 | Matzinger et al. |
| 6,239,445 B1 | 5/2001 | Shaeef |
| 6,335,203 B1 | 1/2002 | Patel et al. |
| 6,441,898 B1 | 8/2002 | Markart |
| 6,599,406 B1 | 7/2003 | Kawanaka et al. |
| 6,645,359 B1 | 11/2003 | Bhullar et al. |
| 6,662,439 B1 | 12/2003 | Bhullar |
| 6,767,440 B1 | 7/2004 | Bhullar et al. |
| 6,770,487 B2 | 8/2004 | Crosby |
| 6,773,671 B1 | 8/2004 | Lewis et al. |
| 6,814,844 B2 | 11/2004 | Bhullar et al. |
| 6,827,829 B2 | 12/2004 | Kawanaka et al. |
| 6,875,327 B1 | 4/2005 | Miyazaki et al. |
| 7,141,212 B2 | 11/2006 | Catt et al. |
| 7,847,946 B2 | 12/2010 | Krauth |
| 2001/0048550 A1 | 12/2001 | Kajiro |
| 2002/0137059 A1 | 9/2002 | Wu et al. |
| 2003/0157726 A1 | 8/2003 | Blum et al. |
| 2003/0207441 A1 | 11/2003 | Eyster et al. |
| 2003/0207454 A1 | 11/2003 | Eyster et al. |
| 2004/0005243 A1 | 1/2004 | Mulhern et al. |
| 2004/0047764 A1 | 3/2004 | Purcell |
| 2004/0200721 A1 | 10/2004 | Bhullar et al. |
| 2004/0247491 A1 | 12/2004 | Brock et al. |
| 2004/0259260 A1 | 12/2004 | Gunstream |
| 2005/0016845 A1 | 1/2005 | Groll et al. |
| 2005/0016846 A1 | 1/2005 | Groll et al. |
| 2005/0019945 A1 | 1/2005 | Groll et al. |
| 2005/0161345 A1 | 7/2005 | Groll et al. |
| 2005/0196747 A1 | 9/2005 | Stiene |
| 2005/0243321 A1 | 11/2005 | Cohen et al. |
| 2005/0279647 A1 | 12/2005 | Beaty |
| 2006/0208199 A1 | 9/2006 | Gallagher |
| 2006/0275182 A1 | 12/2006 | Hudson |
| 2007/0273904 A1 | 11/2007 | Robinson |
| 2007/0292100 A1 | 12/2007 | Yoshikawa |
| 2008/0020452 A1 | 1/2008 | Popovich et al. |
| 2008/0038835 A1 | 2/2008 | Westphal et al. |
| 2008/0105024 A1 | 5/2008 | Creaven |

FOREIGN PATENT DOCUMENTS

| | | |
|---|---|---|
| EP | 1 288 653 A1 | 3/2003 |
| EP | 1 293 926 A2 | 3/2003 |
| EP | 1 484 603 A1 | 12/2004 |
| EP | 1 288 650 A1 | 3/2005 |
| EP | 1 593 961 A1 | 11/2005 |
| WO | WO 97 38126 A1 | 10/1997 |
| WO | WO 02 077620 A1 | 10/2002 |
| WO | WO 2004 113911 A1 | 12/2004 |
| WO | WO 2005 001453 A1 | 1/2005 |
| WO | WO 2006 124917 A2 | 11/2006 |

OTHER PUBLICATIONS

International Search Report corresponding to International Patent Application No. PCT/US2009/061472, European Patent Office, dated Sep. 13, 2009, 8 pages.

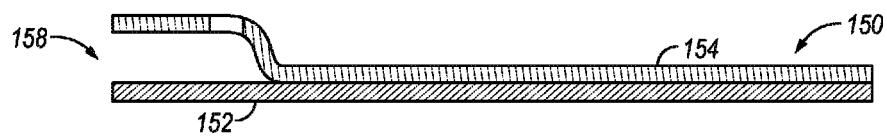
FIG. 2
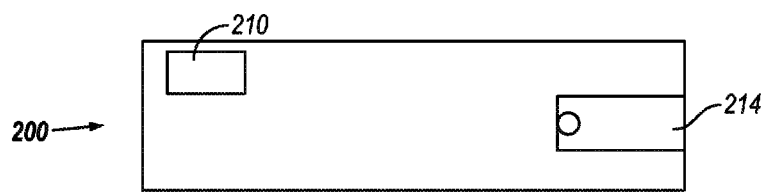
FIG. 3A
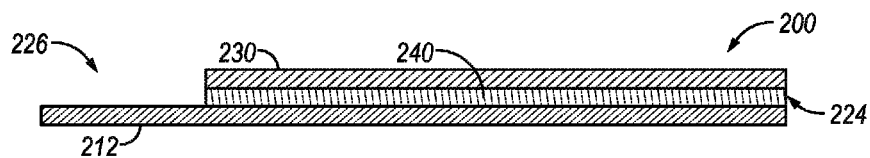
FIG. 3B
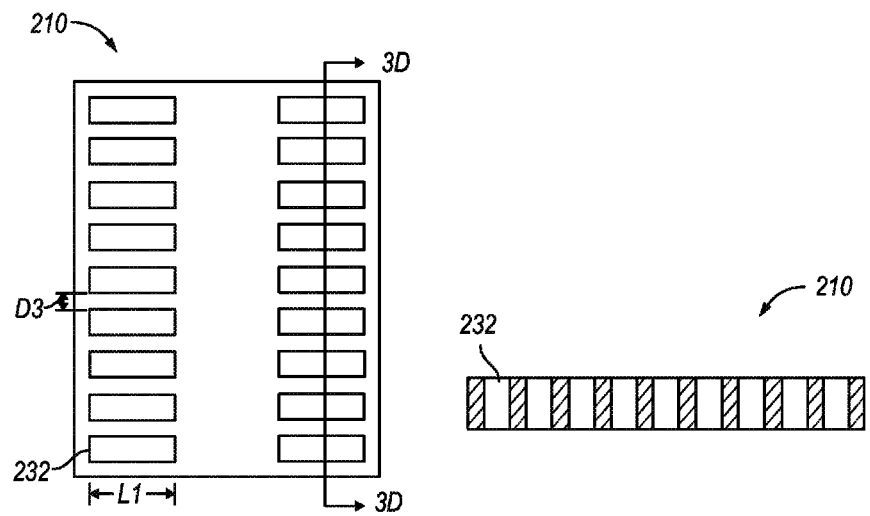
FIG. 3C                    FIG. 3D

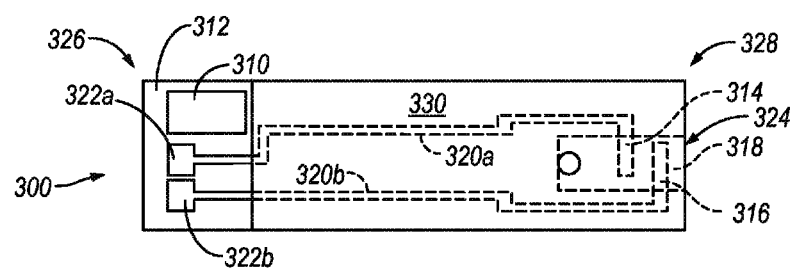
FIG. 4A
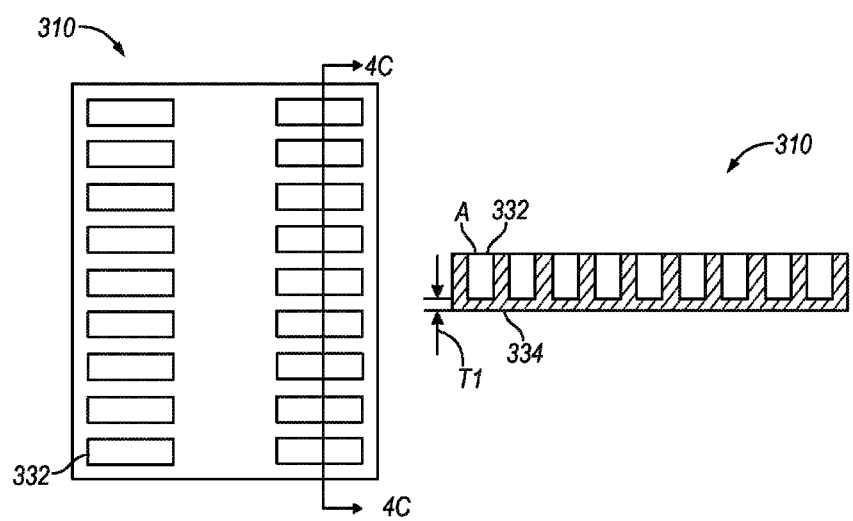
FIG. 4B     FIG. 4C

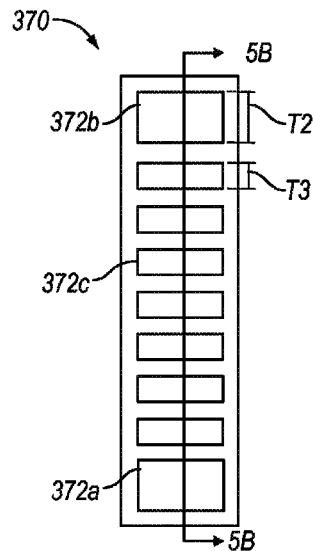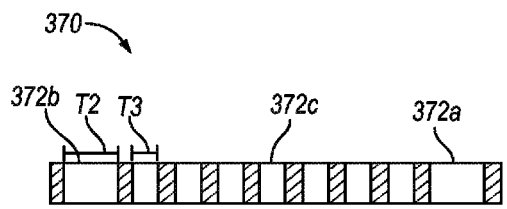
FIG. 5A  FIG. 5B
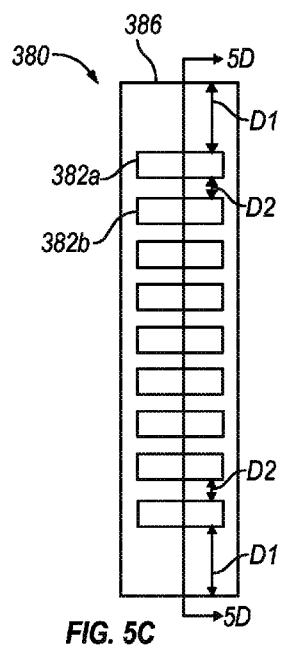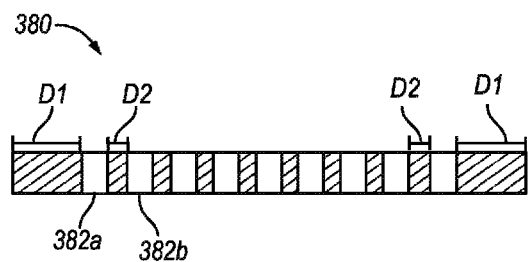
FIG. 5C  FIG. 5D

METHOD OF DETERMINING AUTO-CALIBRATION OF A TEST SENSOR

CROSS-REFERENCE TO RELATED APPLICATIONS

This application is a continuation of application Ser. No. 13/125,126 filed on Apr. 20, 2011, which issued as U.S. Pat. No. 8,586,911 on Nov. 19, 2013; application Ser. No. 13/125,126 filed on Apr. 20, 2011 is a nationalized application of Application No. PCT/US2009/061472 filed on Oct. 21, 2009, which claims the benefit of priority of Provisional Application No. 61/196,859 filed on Oct. 21, 2008, which are all incorporated by reference in their entireties.

FIELD OF THE INVENTION

The present invention generally relates to an optical read head and a method of determining auto-calibration information using an optical read head. The methods are used in automatically calibrating instruments or meters that determine information related to an analyte (e.g., glucose concentration) in a fluid sample.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered. In one type of blood-glucose testing system, sensors are used to test a sample of blood.

A test sensor contains biosensing or reagent material that reacts with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor and the optical system correlates this to information relating an analyte (e.g., glucose) in a fluid sample.

Diagnostic systems, such as blood-glucose testing systems, typically calculate the actual glucose value based on a measured output and the known reactivity of the reagent-sensing element (test sensor) used to perform the test. The reactivity or lot-calibration information of the test sensor may be given to the user in several forms including a number or character that they enter into the instrument. One prior art method included using an element that is similar to a test sensor, but which was capable of being recognized as a calibration element by the instrument. The test element's information is read by the instrument or a memory element that is plugged into the instrument's microprocessor board for directly reading the test element.

These methods suffer from the disadvantage of relying on the user to enter the calibration information, which some users may not do. In this event, the test sensor may use the wrong calibration information and thus return an erroneous result. It is would thus be desirable to provide the mater or instrument the calibration information automatically such that the user would not need to enter this information. It would also be desirable to supply the auto-calibration information in a manner that results in an instrument that is of a desired size (e.g., a low-profile meter) and that is of a desirable low cost.

SUMMARY OF THE INVENTION

According to one method, auto-calibrating information of a test sensor is determined. An optical read head is provided including a light source, a light guide and a detector. The optical read head forms an opening that is sized to receive a test sensor. The detector includes a linear-detector array. A test sensor having a plurality of apertures formed therein is provided. The test sensor is placed in the opening of the optical read head. Light from the light source is transmitted through the plurality of apertures. The light transmitted through the plurality of apertures using the linear-detector array or detecting the absence of light being transmitted through the test sensor using the linear-detector array is detected. The detected light or the absence of detected light information from the detector is used to determine the auto-calibration information of the test sensor.

According to one method, auto-calibrating information of a test sensor is determined. An optical read head is provided including a light source, a light guide and a detector. The optical read head forms an opening that is sized to receive a test sensor. The detector includes a single detector. A test sensor having a plurality of apertures formed therein is provided. The test sensor is placed in the opening of the optical read head. Light is from the light source is transmitted through the plurality of apertures. The light transmitted through the plurality of apertures using the single detector or detecting the absence of light being transmitted through the test sensor using the single detector is detected. The detected light or the absence of detected light information from the detector is used to determine the auto-calibration information of the test sensor.

BRIEF DESCRIPTION OF THE DRAWINGS

FIG. 1b is a side view of the electrochemical test sensor of FIG. 1a.

FIG. 1c is an enlarged top view of the auto-calibration information of FIG. 1a.

FIG. 2 is a cross-sectional view of a test sensor according to another embodiment.

FIG. 3a shows a top view of an optical test sensor according to one embodiment.

FIG. 3b is a side view of the optical test sensor of FIG. 3a.

FIG. 3c is an enlarged top view of the auto-calibration information of FIG. 3a.

FIG. 3d is an enlarged cross-sectional view taken generally across line 3d-3d of FIG. 3c.

FIG. 4a shows a top view of an electrochemical test sensor according to one embodiment.

FIGS. 4b, 4c are enlarged respective top and side views of auto-calibration information of FIG. 4a according to another embodiment.

FIGS. 5a, 5b are enlarged respective top and side views of auto-calibration information according to another embodiment.

FIGS. 5c, 5d are enlarged respective top and side views of auto-calibration information according to a further embodiment.

FIG. 12a is an enlarged top perspective view of the light source, the light aperture component and the plurality of light guides of FIG. 12a, while FIG. 12b is a top perspective view of FIG. 12a.

DETAILED DESCRIPTION OF ILLUSTRATED EMBODIMENTS

Figure 1A:
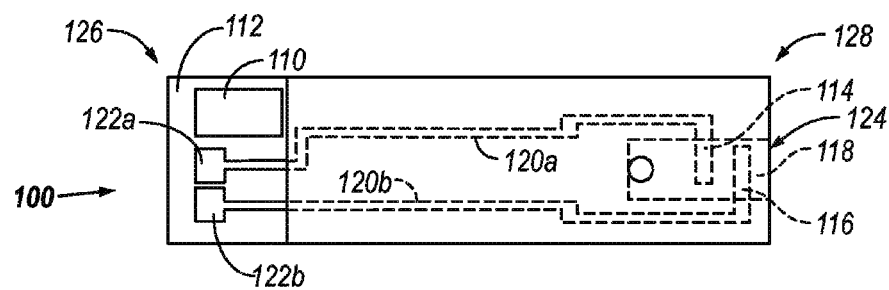
FIG. 1a shows a top view of an electrochemical test sensor according to one embodiment.

An instrument or meter in one embodiment uses a test sensor adapted to receive a fluid sample to be analyzed, and a processor adapted to perform a predefined test sequence for measuring a predefined parameter value. A memory is coupled to the processor for storing predefined parameter data values. Calibration information associated with the test sensor may be read by the processor before the fluid sample to be measured is received. Calibration information may be read by the processor after the fluid sample to be measured is received, but not after the information directed to the analyte has been determined. Calibration information is used in measuring the predefined parameter data value to compensate for different characteristics of test sensors, which are caused by batch-to-batch process variations. Variations of this process will be apparent to those of ordinary skill in the art from the teachings disclosed herein including, but not limited to, the drawings.

The calibration information referred to herein may be any information that is used by a meter or instrument to calibrate. For example, the calibration information may be a program auto-calibration number that relates to a slope, intercept and sensitivity to common interferants of calibration lines for the test-sensor lot or batch.

In addition to defining the calibration information, the present invention may define additional information that has value to the consumer. This information may be transferred from a test sensor to the instrument or meter. The test sensor or test-sensor package may provide expansion capability for future products such as, for example, when the test-sensor chemistries are modified. It is contemplated that other modifications may be implemented. In addition to the calibration information and expansion capability, additional features may be added. For example, information such as market or country information, expiration dates and types of analytes may be transferred from the test sensor to the instrument or meter. The expiration dates may be programmed in different intervals such as, for example, every 2 or 3 months. The expiration date may be used in combination with the date and time of the meter to provide a small, age-related or stress-related correction so as to assist in correcting for an average stability drift. The information may also include detecting counterfeit sensors.

The calibration information is adapted to be formed on a test sensor. The test sensors are used to determine information related to an analyte (e.g., analyte concentrations). Analytes that may be measured include glucose, lipid profiles (e.g., cholesterol, triglycerides, LDL and HDL), microalbumin, hemoglobin $A_{1C}$, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids.

In one embodiment, the test sensors include an appropriately selected enzyme to react with the desired analyte or analytes to be tested. An enzyme that may be used to react with glucose is glucose oxidase. It is contemplated that other enzymes may be used to react with glucose such as glucose dehydrogenase. It is contemplated that other enzymes may be used to react with another analytes.

According to one method, an analyte concentration of a fluid sample is determined using electrical current readings and at least one equation. In this method, equation constants are identified using the calibration information or codes from the test sensor. These constants may be identified by, for example, (a) using an algorithm to calculate the equation constants or (b) retrieving the equation constants from a lookup table for a particular predefined calibration code that is read from the auto-calibration information on the test sensor.

Referring to FIGS. 1a-1e, a test sensor 100 that includes auto-calibration information 110 is depicted in a non-limiting example. The auto-calibration information 110 is in the form of a plurality of apertures 132. The test sensor 100 typically receives a fluid sample and is analyzed using an instrument or meter.

Figure 1B:
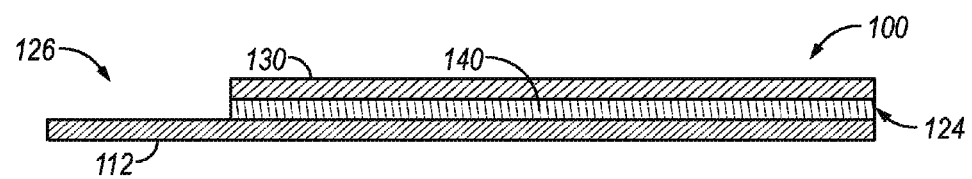

The test sensors described herein may be electrochemical test sensors. In such embodiments, the meter uses optical aspects to detect the calibration information and electrochemical aspects to determine information relating to the analyte (e.g., analyte concentration) of the fluid sample. One non-limiting example of an electrochemical test sensor is shown in FIGS. 1a, 1b. FIGS. 1a, 1b depict the test sensor 100 including a base 112, a channel (e.g., capillary channel), and a plurality of electrodes 114 and 116. A region 118 shows an area that defines the capillary channel (e.g., after a lid 130 is placed over the base 112). The plurality of electrodes includes a counter electrode 114 and a working (measuring) electrode 116. The electrochemical test sensor may also contain at least three electrodes, such as a working electrode, an auxiliary or counter electrode, a trigger electrode, an undefill detection electrode, or a hematocrit electrode. The electrodes 114, 116 are coupled to a plurality of conductive leads 120a, 120b that in the illustrated embodiment terminate with a larger area designated as test-sensor contacts 122a, 122b. The capillary channel is generally located in a fluid-receiving area 124. It is contemplated that other electrochemical test sensors may be employed.

The fluid-receiving area 124 includes at least one reagent for converting the analyte of interest (e.g., glucose) in the fluid sample (e.g., blood) into a chemical species that is electrochemically measurable, in terms of the electrical current it produces, by the components of the electrode pattern. The reagent typically contains an enzyme such as, for example, glucose oxidase, which reacts with the analyte and with an electron acceptor such as a ferricyanide salt to produce an electrochemically measurable species that can be detected by the electrodes. It is contemplated that other enzymes may be used to react with glucose such as glucose dehydrogenase. If the concentration of another analyte is to be determined, an appropriate enzyme is selected to react with the analyte.

A fluid sample (e.g., blood) may be applied to the fluid-receiving area 124. The fluid sample reacts with the at least one reagent. After reacting with the reagent and in conjunction with the plurality of electrodes, the fluid sample produces electrical signals that assist in determining the analyte concentration. The conductive leads 120a, 120b carry the electrical signal back toward a second opposing end 126 of the test sensor 100 where the test-sensor contacts 122a, 122b transfer the electrical signals into the meter. The conductive leads 120a, 120b and test-sensor contacts 122a, 122b are desirably located adjacent to the auto-calibration information 110 so that the optical read head has an unobstructed path for reading the auto-calibration information 110.

Referring specifically to FIG. 1b, a side view of the test sensor 100 of FIG. 1a is shown. As shown in FIG. 1b, the test sensor 100 of FIG. 1b further includes a lid 130 and a spacer 140. The base 112, the lid 130, and the spacer 140 may be made from a variety of materials such as polymeric materials. Non-limiting examples of polymeric materials that may be used to form the base 112, the lid 130, and the spacer 140 include polycarbonate, polyethylene terephthalate (PET), polyethylene naphthalate (PEN), polyimide, and combinations thereof. It is contemplated that other materials may be used in forming the base 112, lid 130, and/or spacer 140.

To form the test sensor 100 of FIGS. 1a, 1b, the base 112, the spacer 140, and the lid 130 are attached by, for example, an adhesive or heat sealing. When the base 112, the lid 130, and the spacer 140 are attached, the fluid-receiving area 124 is formed. The fluid-receiving area 124 provides a flow path for introducing the fluid sample into the test sensor 100. The fluid-receiving area 124 is formed at a first end or testing end 128 of the test sensor 100.

It is contemplated that the test sensors may be formed with a base and a lid in the absence of a spacer. In one such embodiment, a lid may be formed with a convex opening that is adapted to receive a fluid. A non-limiting example of such a test sensor is shown in FIG. 2. Specifically, in FIG. 2, a test sensor 150 includes a base 152 and a lid 154. When the lid 154 is attached to the base 152, a fluid-receiving area 158 is formed that is adapted to receive fluid for testing.

The test sensors to be used in the inventive methods described herein may be optical test sensors. Optical test sensor systems may use techniques such as, for example, transmission spectroscopy, diffuse reflectance, spectroscopy, or fluorescence spectroscopy for measuring the analyte concentration. An indicator-reagent system and an analyte in a sample of body fluid are reacted to produce a chromatic reaction, as the reaction between the reagent and analyte causes the sample to change color. The degree of color change is indicative of the analyte concentration in the body fluid.

Referring to FIGS. 3a, 3b, an optical test sensor 200 is shown. The optical test sensor 200 includes auto-calibration information 210 and a sample-receiving area 214. The sample-receiving area 214 includes an indicator-reagent system that is adapted to produce a chromatic reaction after being exposed to an analyte in a fluid sample. The reagent may be dried and then mixed with the sample in the sample-receiving area. Alternatively, the reagent may be deposited with the sample or after the sample has been received in the sample-receiving area.

Figure 1C:
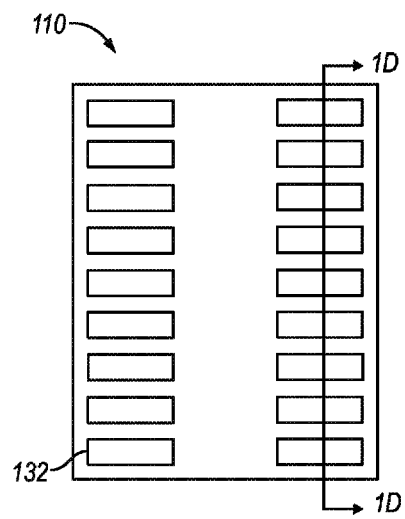
Figure 1D:
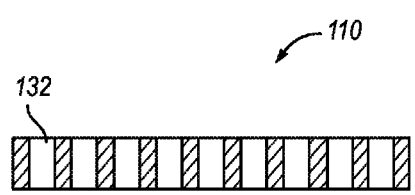
FIG. 1d is an enlarged cross-sectional view taken generally across line 1d-1d of FIG. 1c.
Figure 1E:
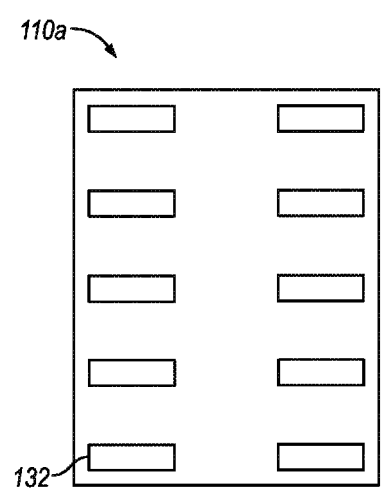
FIG. 1e is a top view of specific auto-calibration information according to one embodiment.

Referring to FIGS. 1c, 3c, the respective test sensors 100, 200 includes respective plurality of apertures 132, 232 formed therein. The respective apertures 132, 232 are also shown as clear (unhatched) areas in respective FIGS. 1d, 3d. In both of FIGS. 1c, 3c, all of the potential apertures in these embodiments have been formed. FIG. 1e depicts one non-limiting example of auto-calibration information 110a using less than all of the potential apertures shown in FIG. 1c. The selection of which apertures to form will convey the specific auto-calibration information to the meter or instrument.

The apertures 132, 232 may be formed by cutting of the test sensors 100, 200. As will be discussed below, the cutting may be performed by lasers, mechanical punching, die cutting or by using water jets. The shape of the apertures 132, 232 is shown as being a thin generally rectangular slit. It is contemplated the shape of the apertures may differ from that depicted in FIGS. 1c, 3c.

Referring to FIGS. 4a-4c, a test sensor 300 is shown that includes auto-calibration information 310. The only difference between test sensor 300 and test sensor 100 is the auto-calibration information area. The auto-calibration information 310 is in the form of a plurality of apertures 332 that extend partially into, but not through, the test sensor 300. Referring specifically to FIG. 4c, after the plurality of apertures 332 is formed, a remaining portion 334 adjacent to the plurality of apertures 332 remains. The remaining portion 334 is formed of a material and a thickness T1 that allows light to be transmitted through and detected on the opposing side. More specifically, the remaining portion 334 is of an optically clear or translucent material that allows light to be transmitted therethrough. Non-limiting examples of optically clear or translucent material that may be used include "white" or clear polyethylene terephthalate (PET), "white" or clear polycarbonate, or "white" or clear glycol-modified PET (PETG). Alternatively, an optically clear or translucent substrate may be covered with an opaque coating that is then selectively removed to form the apertures of FIG. 4c. Examples of such opaque coatings are metals, such as aluminum, gold or copper formed by vacuum deposition, sputtering or plating, and carbon, which may be coated or printed.

Another example of auto-calibration information that may be used in a test sensor is shown in FIGS. 5a, 5b. Auto-calibration information 370 of FIGS. 5a, 5b is shown being formed with a plurality of apertures 372. The auto-calibration information 370 may be used with the above-described test sensors. The auto-calibration information 370 is in one column and apertures 372a, 372b have a thickness or width T2 that is greater than the thickness or width T3 of the remaining apertures (e.g., aperture 372c). By having different thicknesses T2, T3, the optical read head can better identify the beginning and end of the apertures 372 in reading the auto-calibration information.

A further example of auto-calibration information is shown in FIGS. 5c, 5d. Auto-calibration information 380 of FIGS. 5c, 5d is shown being formed with apertures 382. The auto-calibration information 380 may be used with the above-described test sensors. The auto-calibration information is in one column and the distance D1 between an edge 386 of the auto-calibration information 380 and the aperture 382a is different than the distances D2 between the apertures 382 (see, e.g., distance D2 between apertures 382a, 382b). By having different distances D1, D2, the optical read head can better identify the beginning and end of the apertures 382 in reading the auto-calibration information.

The auto-calibration information may be formed on the test sensor by several methods. For example, a laser may form the auto-calibration information on the test sensor. The laser functions by cutting the test sensor at least partially such that light may be transmitted therethrough. In one aspect, the laser cuts entirely through the test sensor such that light is transmitted therethrough. This is shown, for example, in FIGS. 1d and 3d with respective test sensors 100, 200. In another aspect, the laser cuts partially into the test sensor in such a manner that the only remaining portion is a clear or translucent material that allows light to be transmitted therethrough. This is shown, for example, in FIG. 4d with test sensor 300. There are many different types of lasers that may be used in creating the pattern in the test sensor.

One laser that may be used to form the apertures is a solid-state laser such as an yttrium-based laser. Examples of yttrium-based lasers that are commercially available are Rofin DY-HP Series, Telesis ECLIPSE® TLM, or Telesis ZENITH® Series. It is contemplated that other yttrium-based lasers may be used such as Y—$VO_4$ lasers may be used.

Another type of laser that may be used is a gas laser such as a carbon dioxide-based laser. Examples of carbon dioxide-based lasers that are commercially available are Rofin FA Series, Telesis SABRE® Series, or Keyence ML-G Series $CO_2$. It is contemplated that other carbon dioxide-based lasers may be used.

A further type of laser that may be used is an Excimer laser, which uses a mask. Excimer lasers use reactive gases, such as chlorine and fluorine, that are mixed with inert gases such as argon, krypton or xenon. An example of an Excimer laser that is commercially available is Lambda Physik $F_2$ Series. It is contemplated that other Excimer lasers may be used. It is also contemplated that other lasers and other lasers with masks may be used in forming the apertures other than those discussed above in the specific examples above.

It is also contemplated that the apertures may be created using direct writing of the lines. In this method, the laser beam of light is moved so as to form the desired pattern. Non-limiting examples of such lasers are carbon dioxide-based lasers and yttrium-based lasers such as yttrium aluminum garnet (YAG) lasers and Y—$VO_4$ lasers. For example, a beam-steered $CO_2$ laser operating at 10.6 μm may be used to generate coded test strips (i.e., apertures) by cutting short lines that may be of various lengths and distances apart. For example, the length of the apertures (e.g., length L1 of apertures 232 of FIG. 3c) may be about 0.72 mm long and are spaced 0.35 mm apart (e.g., distance D3 in FIG. 3c).

Using lasers is desirable because they are adapted to work in tighter spaces. For example, these laser methods can produce spaces between adjacent electrical areas of from about 1 to about 10 mils, which allows for the possibility of tighter tolerances and/or a smaller auto-calibration area.

The number of rows and columns of the apertures is selected on considerations such as the accuracy of the formation of the apertures (e.g., the placement of the columns and rows), the resolution of the optical detector and the width of the test sensor, and of the capability of the optical system for uniform illumination of the aperture array. This invention allows uniform illumination of a relatively large aperture array, allowing transfer of much information from a read head of compact dimensions. The auto-calibration information of 110, 210, 310 is shown in a generally rectangular array. It is contemplated, however, that the auto-calibration information may be formed in different shapes than depicted in FIGS. 1c, 3c, 4b, 5a, and 5c. For example, the auto-calibration information may be in a square array, other polygonal-shaped arrays, and non-polygonal shapes including circular and oval.

In one method of determining auto-calibrating information of a test sensor, an optical read head is provided. The optical read head includes a light source, a light guide and a detector. The optical read head forms an opening that is sized to receive a test sensor. The detector includes a linear-detector array in one method. A test sensor is provided having a plurality of apertures formed therein. The test sensor is placed in the opening of the optical read head. Light is transmitted from the light source through the plurality of apertures. In one aspect, the transmitted light is detected through the plurality of apertures using the linear-detector array. In another aspect, the absence of light is detected being transmitted through the test sensor using the linear-detector array. The detected light or the absence of detected light information is used from the detector to determine the auto-calibration information of the test sensor.

Figure 6:
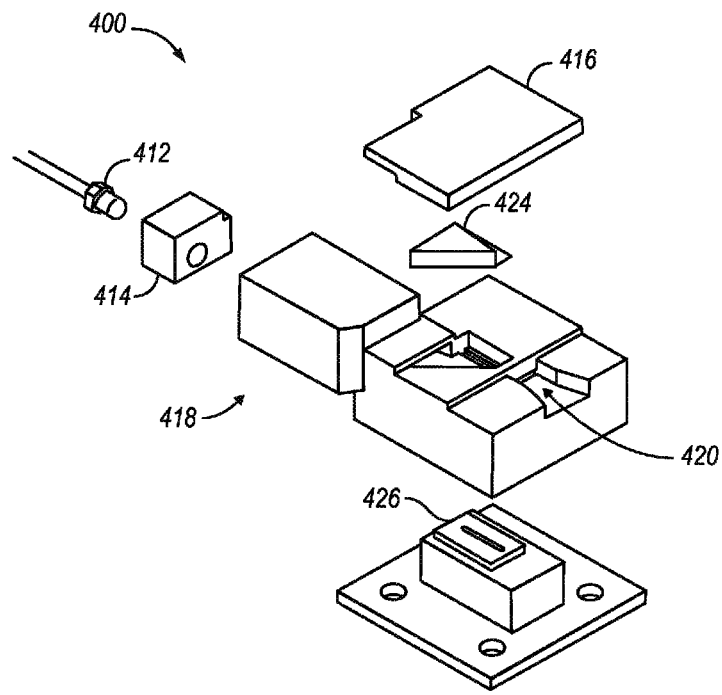
FIG. 6 shows an exploded view of an optical read head according to one embodiment.

The test sensors (e.g., test sensors 100, 200, 300) are adapted to be placed in an optical read head. An example of an optical read head is depicted in FIG. 6. The optical read head 400 of FIG. 6 is adapted to read auto-calibration information from the test sensor. More specifically, the optical read head 400 is adapted to read information regarding the plurality of apertures. The optical read head may be located on a printed circuit board.

Figure 7:
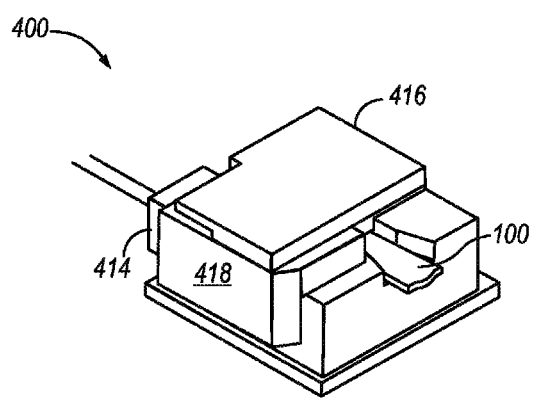
FIG. 7 shows the test sensor of FIG. 1a being inserted into the optical read head of FIG. 6.

The optical read head provides a reliable method of passing this auto-calibration information to the meter or instrument. FIG. 7 shows the test sensor 100 after being inserted into the optical read head 400. The optical read head is typically located within the meter or instrument (e.g., meter 160 of FIG. 8). The optical read head is located in a congested region of the meter that includes the connector that links the meter or instrument with the test sensor.

The optical read head 400 includes a light source 412, a light-source holder 414, a cover 416, housing 418, a light guide 424 and a detector 426. The optical read head 400 is shown in the absence of a lens. It is contemplated that a lens may be included in an optical read head to assist in imaging the test sensor.

The light-source holder 414, cover 416 and housing 418 assist in protecting the components of the optical read head 400. The light-source holder 414, cover 416 and the housing 418 also assist in keeping stray light from the detector. Thus, the light-source holder 414, the cover 416 and the housing 418 are desirable opaque so as to not transmit light. The light-source holder 414, cover 416 and housing 418 may also form apertures that help to improve the intensity uniformity of the beam leaving the light guide 412.

The light-source holder 414 also assists in positioning the light source 412 relative to the light guide 424. More specifically, the light-source holder 414 assists in directing the light to the correct location and locates the light source 412 in the correct placement in the assembly. The housing 418 forms an opening 420 that receives a test sensor and, in some embodiments, the housing 418 holds the electrical contacts that make connection with the test strip to start the testing process.

Specifically, in FIGS. 6 and 7, the light source 412 illuminates a test sensor (e.g., test sensor 100) onto the detector 426. One example of a light source that may be used in the optical read head is a light-emitting diode (LED). LEDs tend to be energy efficient. One example of a LED that may be used is a T1 LED. T1 LED's are available at different wavelengths. One desirable T1 LED includes a wavelength of about 660 nm, which provides desirable power in an economical manner. It is desirable for a T1 LED to have a smaller diameter and length so as to provide a compact light source. One exemplary T1 LED has a diameter less than about 2.5 mm and a length less than about 5 mm. It is contemplated that other light sources may be used such as miniature tungsten lamps.

Having a light guide such as light guide 424 of FIG. 6 is advantageous because it provides for the meter or instrument to have the ability to be designed to have a generally low profile (i.e., a generally thinner meter or instrument). A particular advantage of the light guide 424 is that it allows light from a single source to form a relatively uniformly bright extended beam, which is suitable for illuminating a plurality of apertures. The path of the light from the light source may be a three dimensional path. One non-limiting example of a light guide with a three dimensional path is shown in FIG. 9.

Figure 9:
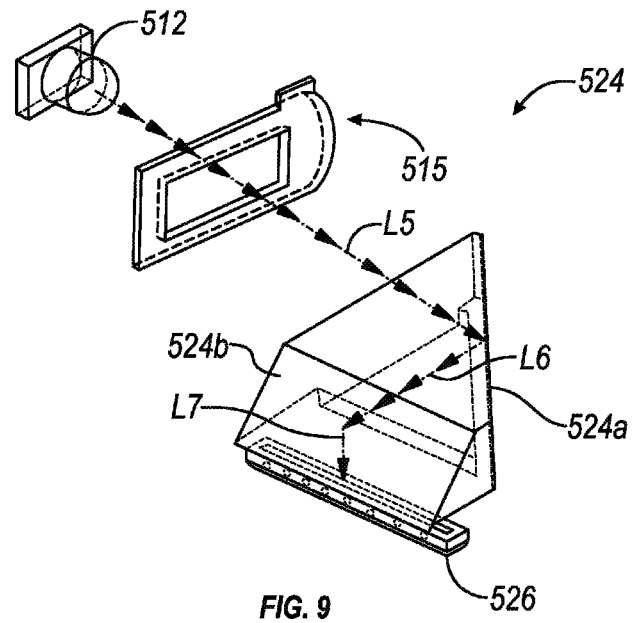
FIG. 9 is an enlarged view of a light source, light aperture component and a light guide depicting a three dimensional path according to one embodiment.

Referring to FIG. 9, an enlarged view of a light source 512, a light aperture component 515, a light guide 524 and a detector 526 are shown. The light guide 524 has a first surface 524a and a second surface 524b to assist in directing the light from the light source 512. The first surface 524a is at an approximately 45 degree angle to incoming light L5. The first surface 524a redirects the incoming light L5 proceeding in a generally horizontal direction to a generally perpendicular direction in the same plane (light L6) as shown in FIG. 9 where the length of this surface determines the length of the beam exiting the light guide and the height or thickness of the light guide determines the width of the beam. The light L6 is directed to the second surface 524b, which is also at an approximately 45 degree angle to the light L6. The light L6 is then redirected in a generally vertical direction (shown as light L7 in FIG. 9).

Figure 10:
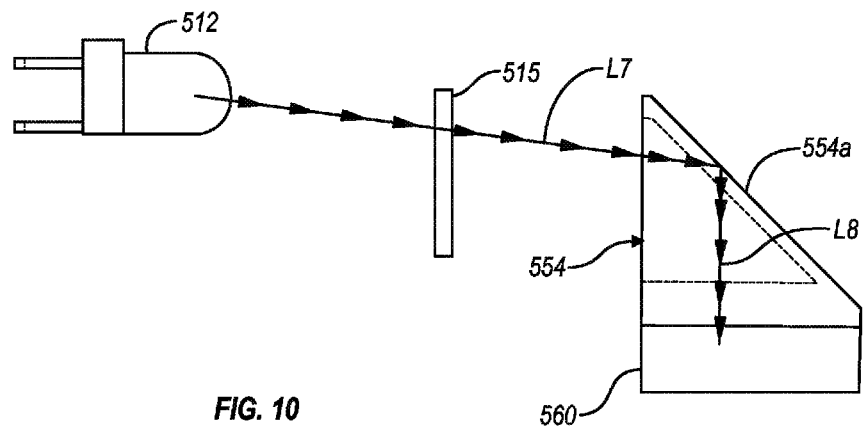
FIG. 10 is an enlarged view of a light source, light aperture component and a light guide depicting a two dimensional path according to one embodiment.
Figure 11:
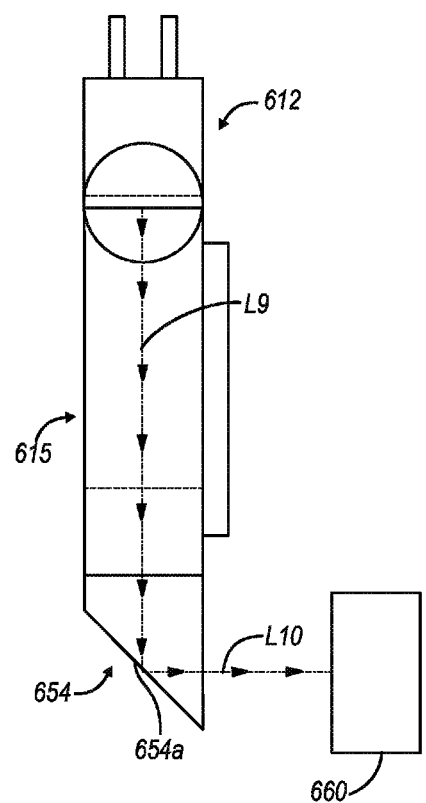
FIG. 11 is an enlarged view of a light source, light aperture component and a light guide depicting a two dimensional path according to another embodiment.

In another aspect, the path of the light from the light source may be a two dimensional path. Non-limiting examples of light guides with a two dimensional path are shown in FIGS. 10, 11. Referring initially to FIG. 10, an enlarged view of a light source 512, a light-aperture component 515, a light guide 554 and a detector 560 are shown. The light guide 554 has a first surface 554a to assist in directing the light from the light source 512. The first surface 554a is at an approximately 45 degree angle to incoming light L7. The first surface 554a redirects the incoming light L7 proceeding in a generally horizontal direction to a generally downwardly direction (light L8) as shown in FIG. 10. The light L8 is directed to the detector 560.

Referring to FIG. 11, an enlarged view of a light source 612, a light-aperture component 615, a light guide 654 and a detector 660 are shown. The light guide 654 has a first surface 654a to assist in directing the light from the light source 612. The first surface 654a is at an approximately 45 degree angle to incoming light L9. The first surface 654a redirects the incoming light L9 proceeding in a generally horizontal direction to a generally perpendicular direction in the same plane (light L10) as shown in FIG. 11. The light L10 is directed to the detector 660.

Figure 12A:
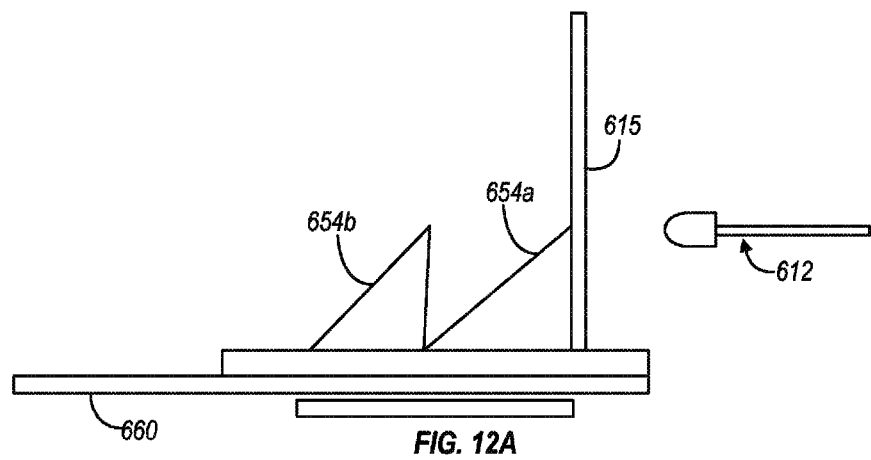
FIG. 12a is an enlarged side view of a light source, light aperture component and a plurality of light guides depicting a two dimensional path according to another embodiment.
Figure 12B:
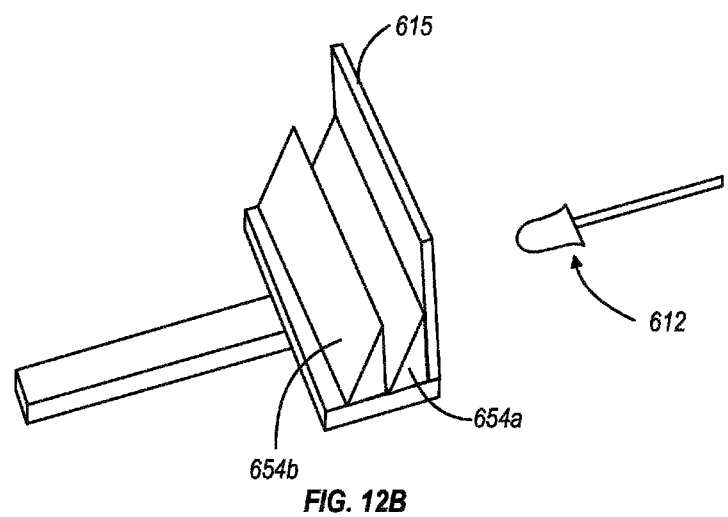

A limitation of a two-dimensional light guide is that as the length of the aperture-illuminating beam is determined by the length of the first surface 554a of FIG. 10, it may be difficult to illuminate a long array with a compact read head. The difficulty will be dependent on, for example, the height of the light guide. FIGS. 12a, 12b illustrates two, two-dimensional read heads placed one behind the other and angled slightly so as to double the length of the illuminating beam without increasing the overall height of the read head.

Specifically, FIGS. 12a, 12b illustrate a light source 612, light-aperture component 615, a plurality of light guides 654a, 654b and a detector 660. The light guides 654a, 654b have respective first surfaces that assist in directing the light from the light source 612. The first surfaces are at an approximately 45 degree angle to incoming light and redirect that light in a generally downwardly direction. The first surfaces redirect the incoming light from light source 612 proceeding in a generally horizontal direction to a generally perpendicular direction. The redirected light is directed to the detector 660.

It is contemplated that the light guide may include additional reflecting surfaces therein to allow placement of the light source to be optimized with respect to other components of the meter or instrument.

The light guide is desirably positioned above the apertures formed in the auto-calibration information after the test sensor has been inserted. The apertures formed in the auto-calibration information are desirably directly above detector after the test sensor has been inserted.

In one aspect, the light guide may be a polymeric material (e.g., an acrylate) that includes a polished surface to assist in redirecting the light. The polished surface may be, for example, a diamond-polished surface. In another aspect, the light guide may be a mirror that assists in redirecting the light. It is desirable for the light guide to redirect a substantial amount, if not all, of the light coming from the light source.

It is also contemplated that the light may be further directed by the light guide to a front of the meter or instrument so as to illuminate the region in front of the meter or instrument. This may be especially useful if a user is collecting fluid or placing the test sensor into the opening under poor lighting conditions.

One example of a detector that may be used in the optical read head 400 is a linear-array detector. A linear-array detector may be used to read all of the auto-calibration information at one time because the length of the detector is longer than the auto-calibration code. By using a static reading of all of the auto-calibration information at once, more auto-calibration information may be potentially read without misreading errors that tend to accompany systems where the sensor is being decoding during insertion of the test sensor into the meter. One commercial example of a linear-array detector is a TAOS model TSL 1401R 128 channel linear-sensor array detector marketed by Texas Advanced Optoelectronic Solutions (TAOS), Inc. of Plano, Tex. This linear-array detector has 128 discrete detectors.

In one process, the apertures (e.g., apertures 132 of FIGS. 1c, 1d) of the auto-calibration information are uniformly illuminated and the aperture pattern is transmitted directly on a matching linear-array detector having a plurality of contiguous detectors or pixels. The number of contiguous detectors may vary in the linear-sensor array. Typically, the number of contiguous detectors is from about 16 to about 512 and, more specifically, from about 32 to about 128.

It is contemplated that a plurality of detectors may be used that is shorter than the length of the auto-calibration code in which the test sensor is scanned when inserted into the meter or instrument. This is advantageous in that a much smaller and less expensive detector array can be used because it only has to scan and report on the columns of the aperture array. In this approach, the light guide and the detector array may be mounted in the same orientation such that the illuminating beam and the detector array are located along the short direction of the sensor. A subset of the detector array is aligned with each column, and as the sensor is moved into the read head this subset reports on the row of apertures in this column of apertures.

Figure 13:
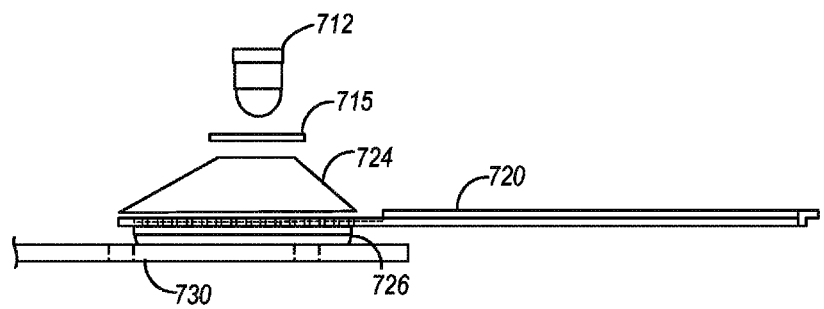
FIG. 13 is an enlarged view of a light source, light aperture component and a light guide depicting a generally one dimensional path according to one embodiment.

One non-limiting example of such a light guide and a detector is shown in FIG. 13. FIG. 13 depicts an enlarged view of a light source 712, a light aperture component 715, a light guide 724 and a detector 726 are shown. The light guide 724 assists in directing the light from the light source 712 onto test sensor 720 and eventually the detector 726. The detector 726 may be mounted on a surface such as printed circuit board 730 shown in FIG. 13.

In another aspect, the detector may include a single detector. One non-limiting detector that may be used is a silicon detector having only one active-detection area. By having a single detector, the auto-calibration information is read or decoded as the test sensor is being inserted into the meter or instrument. The detectors (e.g., detector 426 of FIG. 6) shown in the Figures may be the above-described linear-array detector or single detector.

If an optical read head is used in combination with an optical test sensor, in addition to detecting the auto calibration information, the optical read head may assist in determining the concentration of an analyte. Specifically, the optical read head may be used to detect a photometric color change in the reactant area of the test sensor. In this embodiment, the optical read head is bi-functional.

The optical read head typically has a thickness of from about 0.1 inch to about 0.2 inch and, more specifically, from about 0.125 to about 0.175 inch or even more specifically from about 0.155 to about 0.165 inch. By having such an optical read head thickness, a meter or instrument may be developed that is a low-profile meter or instrument.

Figure 8:
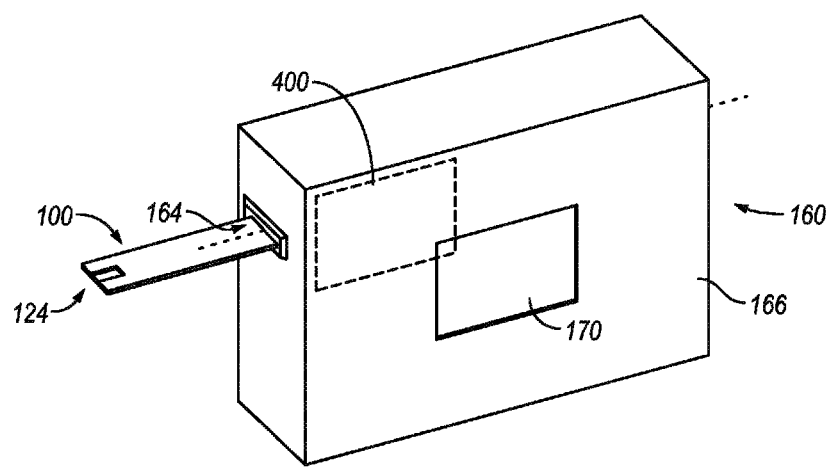
FIG. 8 is an isometric view of an instrument or meter according to one embodiment that includes the optical read head of FIG. 7 and is adapted to receive a test sensor.

Referring back to FIGS. 1a, 1b, the second opposing end 126 of the test sensor 100 is adapted to be placed into a test-sensor opening 164 in the instrument or meter 160 of FIG. 8. The meter 160 includes a housing 166 that forms the test-sensor opening 164, which is of sufficient size to receive the second opposing end 126 of the test sensor 100. After entering the test-sensor opening, the test sensor continues and is located within an opening of the optical read head. After the calibration information of the test sensor 100 has been determined using the optical read head 400, the meter 160 uses, for example, the appropriate program number during calculation of the analyte concentration by the meter software. The housing 166 may comprise a display 170 (e.g., an LCD screen) that displays, for example, analyte concentrations.

In the embodiments described herein, the test sensors are desirably fully inserted into the test-sensor opening for the calibration information to be correctly ascertained. Thus, the meters used with the test sensors may include a mechanism for determining whether the test sensors are fully inserted. The mechanism may be positioned, for example, in or adjacent to the test-sensor opening. The meter may further be adapted to report an error to a user if it detects that the test sensor is not fully inserted.

The instrument may include several responses to reading the auto-calibration information. For example, responses may include the following codes: (1) correct read, (2) misread, (3) non-read, defective code, (4) non-read, missing calibration information, and (5) read code out-of-bounds. A correct read indicates that the instrument or meter correctly read the calibration information. A misread indicates that the instrument did not correctly read the calibration information. A non-read, defective code indicates that the instrument senses that auto-calibration information is present, but the information fails one or more encoding rules. A non-read, missing auto-calibration information indicates that the instrument does not sense the presence of auto-calibration information. A read code out-of-bounds indicates that the instrument senses an auto-calibration code, but the calibration information is not valid for that instrument.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention.

What is claimed is:

1. A method of determining auto-calibrating information of a test sensor, the method comprising the acts of:
providing an optical read head, the optical read head including a light source, a light guide and a detector, the optical read head forming an opening that is sized to receive a test sensor, the detector including a linear-detector array;
providing a test sensor having a plurality of apertures formed therein;
placing the test sensor in the opening of the optical read head;
transmitting light from the light source through the plurality of apertures;
detecting the light transmitted through the plurality of apertures using the linear-detector array or detecting the absence of light being transmitted through the test sensor using the linear-detector array; and
using the detected light or the absence of detected light information from the detector to determine the auto-calibration information of the test sensor.

2. The method of claim 1 wherein the transmitted light is detected through the plurality of apertures using the linear-detector array.

3. The method of claim 1 wherein the absence of light being transmitted through the test sensor is detected using the linear-detector array.

4. The method of claim 1 wherein the light guide transmits the light from an initially generally horizontal direction and redirects the light in a generally vertical direction onto the plurality of apertures of the test sensors.

5. The method of claim 1 wherein the light guide transmits the light from an initially generally horizontal direction and redirects the light in a generally perpendicular direction in the same plane and then redirects the light in a generally vertical direction.

6. The method of claim 1 wherein the test sensor is an optical test sensor.

7. The method of claim 1 wherein the test sensor is an electrochemical test sensor.

8. The method of claim 1 wherein the plurality of apertures extends completely through the test sensor.

9. The method of claim 1 wherein the plurality of apertures extends partially into the test sensor and wherein the light from the light source is transmitted and detected through an optically clear or translucent material.

10. A method of auto-calibrating a test sensor, the method comprising the acts of:
providing an optical read head, the optical read head including a light source and a detector, the optical read head forming an opening that is sized to receive a test sensor, the detector including a single detector;
providing a test sensor having a plurality of apertures formed therein;
placing the test sensor in the opening of the optical read head;
transmitting light from the light source through the plurality of apertures;
detecting the light transmitted through the plurality of apertures using the single detector or detecting the absence of light being transmitted through the test sensor using the single detector; and using the detected light or the absence of detected light information from the detector to determine the auto-calibration information of the test sensor.

11. The method of claim 10 wherein the transmitted light is detected through the plurality of apertures using the single detector.

12. The method of claim 10 wherein the absence of light being transmitted through the test sensor is detected using the linear-detector array.

13. The method of claim 10 wherein the light guide transmits the light from an initially generally horizontal direction and redirects the light in a generally vertical direction onto the plurality of apertures of the test sensors.

14. The method of claim 10 wherein the light guide transmits the light from an initially generally horizontal direction and redirects the light in a generally perpendicular direction in the same plane and then redirects the light in a generally vertical direction.

15. The method of claim 10 wherein the test sensor is an optical test sensor.

16. The method of claim 10 wherein the test sensor is an electrochemical test sensor.

17. The method of claim 10 wherein the plurality of apertures extends completely through the test sensor.

18. The method of claim 10 wherein the plurality of apertures extends partially into the test sensor and wherein the light from the light source is transmitted and detected through an optically clear or translucent material.

* * * * *